United States Patent [19]

Throckmorton

[11] 3,932,508

[45] Jan. 13, 1976

[54] POLYFLUOROMETHYLTHIO-SUBSTITUTED COMPOUNDS

[75] Inventor: James R. Throckmorton, Woodbury, Minn.

[73] Assignee: Minnesota Mining and Manufacturing Company, St. Paul, Minn.

[22] Filed: Apr. 26, 1974

[21] Appl. No.: 464,493

[52] U.S. Cl.... 260/566 AC; 260/566 A; 260/593 H; 424/327
[51] Int. Cl.$^2$........................................ C07C 131/00
[58] Field of Search...... 260/566 A, 566 AC, 593 H

[56] References Cited
UNITED STATES PATENTS

| | | | |
|---|---|---|---|
| 3,299,137 | 1/1967 | Payne et al................... | 260/566 AC |
| 3,454,642 | 7/1969 | Friedman..................... | 260/566 AC |

FOREIGN PATENTS OR APPLICATIONS 7,204,698    1973    Netherlands

OTHER PUBLICATIONS

Sandler et al., "Organic Functional Group Preparations" Vol. III pp. 150–151 (1972).
Chemical Abstracts Vol. 79 66238(w) (1973) (Bayreuther et al.).

*Primary Examiner*—Gerald A. Schwartz
*Attorney, Agent, or Firm*—Alexander, Sell, Steldt & DeLaHunt

[57] ABSTRACT

The compounds 1-trifluoromethylthio-3,3-dimethyl-2,butanone-O-methylcarbamoyloxime and 1-difluoromethylthio-3,3-dimethyl-2-butanone-O-methylcarbamoyloxime are prepared from certain novel ketone and oxime intermediates. These compounds have insecticidal activity and are particularly effective against the Western and Northern corn rootworms, *Diabrotica virgifera* and *Diabrotica longicornis* respectively.

3 Claims, No Drawings

POLYFLUOROMETHYLTHIO-SUBSTITUTED COMPOUNDS

BACKGROUND OF THE INVENTION

This invention relates to polyfluoromethylthio-substituted ketones and oximes, as intermediates, and to their insecticidal derivatives, polyfluoromethylthio-substituted carbamoyloximes. A further aspect of the invention relates to a process for preparing these compounds. A still further aspect of the invention relates to insecticidal formulations comprising the carbamoyloxime compounds of the invention and to a method of combating insects, especially the corn rootworm, by contacting them with an insecticidal amount of these compounds.

PRIOR ART

Mono- and poly(alkylthio) ketones have been reported previously. For example by Brintzinger et al., Chemical Ber. 87, 300 (1954). This reference describes the reaction of acetone with ethanesulfenyl chloride to produce hexakis-[ethylthio] acetone. Fuson et al., (J. Org. Chem. 11, 469, 1946) have reported the synthesis of a chloralkylthio-substituted ketone by the reaction of acetone with chloroethanesulfenyl chloride.

Neither of the above references suggest the possibility of reacting a polyfluorinated alkanesulfenyl chloride with tert-butylmethyl ketone to produce the polyfluoromethylthio-substituted ketone intermediates of the present invention. This reaction was unexpected in view of the fact that attempts to react nonfluorinated alkanesulfenyl chloride, i.e. methane-sulfenyl chloride, with tert-butylmethyl ketone were unsuccessful. In addition, known reactions of alkanesulfenyl chloride with ketones e.g. acetone, tend to produce poly-substituted alkylthio ketones, e.g. hexalkylthio-substituted acetone, whereas the reaction of polyfluoromethanesulfenyl chlorides with tert-butylmethyl ketone shows little tendency to form polysubstituted products.

A recent publication by Bayreuther and Haas, Chem. Ber., 106, 1418 (1973) describes the preparation of certain trifluoromethylthio-ketones by reaction of the unsubstituted ketone with trifluoromethanesulfenyl chloride. However, prior to the present invention, it is believed that the polyfluoromethylthio-ketone intermediates of the present invention have not been disclosed.

Magee (U.S. patent applications Serial Nos. 132,584 and 229,207) has reported a large group of carbamate derivatives of ketoximes which have pesticidal activity. A number of these carbamate derivatives contain alkylthio-substituents, and the compound 1-methylthio-3,3-dimethyl-2-butanone-0-methylcarbamoyloxime is specifically disclosed. The fluorinated compound 1-(3,3,3-trifluoropropylthio)-3,3-dimethyl-2-butanone-0-methylcarbamoyloxime is also disclosed by this reference. While the above compounds of the prior art are structurally related to the carbamate compounds of the present invention, they do not show significant insecticidal activity against the Western and Northern corn rootworms, whereas the carbamate compounds disclosed herein possess unusually high insecticidal activity against this particularly bothersome pest. In addition, the carbamate compounds disclosed by Magee are prepared according to a different method than that utilized for the preparation of the compounds of the present invention.

DESCRIPTION OF THE INVENTION

Compounds of the present invention can be represented by the formula:

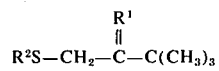

wherein $R^1$ is oxygen, NOH or

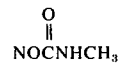

and $R^2$ is —$CF_3$ or —$CF_2H$, and include the following six compounds:

1-difluoromethylthio-3,3-dimethyl-2-butanone
1-trifluoromethylthio-3,3-dimethyl-2-butanone
1-difluoromethylthio-3,3-dimethyl-2-butanone oxime
1-trifluoromethylthio-3,3-dimethyl-2-butanone oxime
1-difluoromethylthio-3,3-dimethyl-2-butanone-O-methylcarbamoyloxime
1-trifluoromethylthio-3,3-dimethyl-2-butanone-O-methylcarbamoyloxime.

Compounds of the invention wherein $R^1$ is oxygen are ketones and can be readily prepared by reacting the unsubstituted ketone with the appropriate polyfluoromethylsulfenyl chloride in an inert solvent. 1-difluoromethylthio-3,3-dimethyl-2-butanone is prepared by reaction of 3,3-dimethyl-2-butanone with difluoromethanesulfenyl chloride, and 1-trifluoromethylthio-3,3-dimethyl-2-butanone is prepared by reaction of 3,3-dimethyl-2-butanone with trifluoromethanesulfenyl chloride. The molar ratio of ketone to sulfenyl chloride can range from about 2:1 to about 1:2, but preferably equimolar amounts of starting materials are used. Excess polyfluoromethanesulfenyl chloride is not detrimental since significant polysubstitution does not readily occur.

The presently preferred solvents for carrying out the above reaction are chlorinated hydrocarbons such as chloroform, dichloromethane and the like. Other suitable solvents are acetonitrile, ethyl acetate, and methyl acetate. Benzene and nitromethane have also been used with some success. It is presently preferred to add as a catalyst small amounts, e.g. less than ten mole percent with respect to the reactants, of an alcohol such as methanol, ethanol, isopropanol or n-hexanol. The effect of the catalyst is to increase the rate and yield of the reaction.

The temperature of the reaction mixture may range from about −78°C. to the reflux temperature of the reaction mixture, i.e. up to about 125°C. The preferred temperature range is about −25° to +50°C.

The reaction may be run in a pressure reactor to provide safer and more efficient confinement of the reactants.

Purification and isolation of the liquid ketone produce is generally carried out by distillation and/or vapor phase chromatography.

The oxime intermediates of the invention are prepared by reacting the polyfluoromethylthio-ketones with hydroxylamine, generally as the hydrochloride. This reaction is carried out in a suitable solvent such as an aqueous alcohol, e.g. ethanol, a halogenated hydrocarbon, e.g. dichloromethane, and the like. The oximination is generally carried out in the presence of an acid acceptor which is typically an organic base, such as a tertiary amine, e.g. triethylamine, or an inorganic base such as sodium carbonate.

Isolation of the solid oxime products is carried out using standard synthetic techniques such as extraction or column chromatography followed by recrystallization or vacuum distillation.

The carbamoyloxime compounds of the invention are obtained from conversion of the oximes. Two convenient methods are available to effect this conversion.

The most preferred method for converting the oximes to the carbamoyloximes consists of reacting the oxime with methyl isocyanate herein termed Process A. This reaction is carried out in an inert organic solvent and preferably in the presence of a tertiary amine catalyst. The inert organic solvents which can be employed in the reaction are those which are generally inert to isocyanates, i.e. free of substituents such as amino or hydroxy groups. Examples of useful solvents are aliphatic ketones such as acetone; aliphatic and aromatic hydrocarbons such as hexane, benzene, heptane, octane, toluene and the like; ethers such as diethyl ether and ethyl n-propyl ether; and chlorinated hydrocarbons such as dichloromethane. Suitable catalysts are aliphatic and/or aromatic tertiary amines such as N,N-dimethylaniline, triethylamine or the like. Generally, amounts of tertiary amine catalyst ranging from about 0.1 to about 1.0 weight percent of the starting materials comprised of the oxime and methyl isocyanate are sufficient.

The reaction may be effected at temperatures ranging from 10° to about 130°C. and is preferably carried out between 25° and 90°C. The pressure used is generally one atmosphere, although the reaction can be run at higher pressures if desired.

The mole ratio of isocyanate to oxime can range from about 0.25:1 to about 2:1, but preferably an equimolar amount or slight excess of the isocyanate is employed to insure that the oxime is completely reacted. The reaction time for substantial completion may vary from about 5 minutes to about 7 days, depending upon the reaction temperature and the amount of oxime used. Normally when operating in the preferred temperature range, reaction times of from about ½ hour to about 3 days are sufficient for complete reaction.

An alternative method, herein termed Process B, may be used to convert the oxime compounds to carbamoyloximes and consists of reacting the oxime with phosgene in an inert solvent such as toluene or diethyl ether in the presence of an acid acceptor which is preferably a tertiary amine, e.g. N,N-dimethyl aniline, trimethylamine, triethylamine or the like. The molar ratio of oxime to phosgene is approximately 1:1, and the amount of acid acceptor which is added is approximately equimolar with respect to the other reactants. This reaction can be carried out at from −30°C. to about 40°C., but will generally be found to proceed most advantageously between −10° and 25°C. The reaction is slightly exothermic so that some external cooling is usually necessary to maintain the temperature within the desired range. The reaction mixture can be filtered or washed with water to remove the by-product amine hydrochloride and the organic layer containing the chloroformate can then be further reacted with methylamine. The reaction of the chloroformate intermediate with methylamine is carried out in the presence of a suitable solvent for the intermediate such as diethyl ether, dioxane, toluene or chloroform, at temperatures between about −40° and about 90°C. Preferably the temperature is maintained below about 40°C. because the reaction proceeds smoothly even at low temperatures and is so rapid about 40°C. that loss of low boiling reactants may occur and some decomposition may take place.

The carbamoyloxime products formed by either Process A or Process B are solids which can be recovered from the reaction mixture by means known to the art, such as extraction or vacuum distillation to remove the solvent.

In addition to their especially advantageous activity against the Western and Northern corn rootworms, i.e. *Diabrotica virgifera* and *Diabrotica longicornis*, respectively, compounds of the present invention have been found to be effective against houseflies, mosquitos, and German cockroaches. The compound 1-difluoromethylthio-3,3-dimethyl-2-butanone-0-methylcarbamoyloxime is particularly effective in combating corn rootworms because of its prolonged duration of activity in the soil.

The pesticidal activity of the carbamate compounds of the present invention has been established by standard screening and field tests. These compounds also exhibit activity as plant growth regulators.

The carbamoyloxime compounds of this invention may be applied as insecticides according to methods known to those skilled in the art. Pesticidal compositions containing the compounds as active toxicants will usually comprise a carrier or diluent, either liquid or solid.

Liquid concentrates may be prepared by dissolving the active compound in a solvent such as acetone or xylene and then dispersing the toxicant in water with the aid of suitable surface active agents, i.e., depending and emulsifying agents.

The choice of dispersing and emulsifying agents and the amount of each which is employed is dictated by the nature of the composition and the ability of the agent to facilitate the dispersion of the toxicant. Generally, it is desirable to use as little of the agent as possible, consistent with the desired dispersion of the toxicant in the spray, so that rain does not re-emulsify the toxicant after it is applied to the plant and wash it off the plant. Nonionic, anionic or cationic surface active agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carriers such as clay, talc, bentonite, diatomaceous earth, charcoal, corn cob granules, fullers earth and the like. In the formulation of the wettable powders, the aforementioned surface active agents as well as lignosulfonates can be included.

The formulations are applied in amounts which contain from about one-fourth to 15 pounds of active toxicant per acre. The required amount of the toxicants may be applied in from 1 to 200 gallons or more of water as diluent or in from about 5 to 500 pounds of inert solid carrier as diluent for each acre treated. The concentration of the active ingredient in the liquid concentrate will usually vary from about 5 to 30 percent by weight, and in the solid formulations from about 20 to about 80 percent by weight.

The pesticides described herein prevent attack by insects upon plants or other material to which the pesticide is applied, and they have high residual toxicity. With respect to plants, these pesticides have a high margin of safety in that when used in sufficient amounts to kill or repel the insects, they do not burn or injure the plant. The toxicants are sufficiently chemically inert that they are compatible with substantially any other constituent of the spray schedule, and they may be used in the soil or upon the seeds or roots of plants without injury to the seeds or roots. Furthermore, properties of the compounds are such that they are not unacceptably hazardous to the user.

The invention will be further understood by reference to the following illustrative and nonlimiting examples. All melting points and boiling points given are uncorrected.

EXAMPLE 1

Preparation of 1-difluoromethylthio-3,3-dimethyl-2-butanone

Chlorine (3 moles) was added over a 3-hour period to benzyl difluoromethyl sulfide (3 moles) in dichloromethane at −5° to 5°C. The reaction mixture was then allowed to warm to about 22°C. and then heated at 30°C. for 1 hour. The reaction mixture was cooled to 10° to 20°C., and 3,3-dimethyl-2-butanone (3 moles) and ethanol (2.5 g) was added over a 45 minute period. After 6 hours the reaction mixture was allowed to warm to 25°C. and then heated at 30 to 35°C. for 6 to 7 hours.

Trimethylamine (6 mole, 25% by volume in methanol) was added rapidly to the reaction mixture, and after stirring for 2½ hours at about 22°C., the reaction mixture was heated for 2 hours at 35° to 40°C. The reaction mixture was then washed with water, dried over anhydrous calcium sulfate and distilled to give 1-difluoromethylthio-3,3-dimethyl-2-butanone, b.p. 54° to 61°C./1.8 - 2.5 mmHg. The structure of a pure sample, b.p. 60°C./3 mmHg was confirmed by elemental and spectroscopic analyses.

Calculated for $C_7H_{12}F_2OS$: %C, 46.13; %H, 6.63; Found: %C, 46.6; %H, 6.5.

EXAMPLE 2

Preparation of 1-difluoromethylthio-3,3-dimethyl-2-butanone oxime

A mixture of 1-difluoromethylthio-3,3-dimethyl-2-butanone (2.21 moles) from example 1, hydroxylamine hydrochloride (2.44 moles) and sodium carbonate (1.22 moles) in aqueous ethanol (1 liter of water and 2.3 liters of ethanol) was heated at its reflux temperature for 7.5 hours. This reaction mixture was poured into water, and the product was extracted into diethyl ether. The ether was washed with water and dried, then the ether extracts were evaporated under reduced pressure leaving a residue of 1-difluoromethylthio-3,3-dimethyl-2-butanone oxime. A pure sample, m.p. 92° to 95°C., was obtained by recrystallization from a mixture of diethyl ether and petroleum ether (b.p. 30° to 60°C.).

Analysis: Calculated for $C_7H_{13}F_2NOS$: %C, 42.62; %H, 6.64; %N, 7.09; Found: %C, 42.9; %H, 6.7; %N, 7.2.

EXAMPLE 3

Preparation of 1-difluoromethylthio-3,3-dimethyl-2-butanone-0-Methyl-carbamoyloxime (Process A)

A mixture of 1-difluoromethylthio-3,3-dimethyl-2-butanone oxime (2.03 moles) from example 2, methyl isocyanate (2.4 moles) and triethylamine (15 drops) in 1500 ml. of dichloromethane was refluxed for 60 hours. The solvent was removed by evaporation under reduced pressure. The residual material was recrystallized first from a mixture of diethyl ether and petroleum ether (b.p. 30° to 60°C.) and then from benzene to give a purified sample of 1-difluoromethylthio-3,3-dimethyl-2-butanone-0-methylcarbamoyloxime, m.p. 54° to 56°C. The structure of the product was confirmed by elemental and spectral analyses.

Analysis: Calculated for: $C_9H_{16}F_2N_2O_2S$: %C, 42.50; %H, 6.34; %N, 11.02; Found: %C, 42.8; %H, 6.1; %N, 11.1.

EXAMPLE 4

Preparation of 1-trifluoromethylthio-3,3-dimethyl-2-butanone

A mixture of 3,3-dimethyl-2-butanone (1.13 mole), ethanol (1.5 g.) and dichloromethane (300 ml) was introduced into a sealed and pressure tested 2-liter vessel under reduced pressure. Trifluoromethanesulfenyl chloride (1.05 mole) was then added to the cooled, evacuated vessel. (Caution: It should be noted that trifluoromethanesulfenyl chloride is a highly hazardous material which must be handled with care to avoid inhalation and contact with the skin.) The vessel was warmed to about 25°C. and then rocked for 2½ to 3 days. The vessel was vented through a cold gas trap (−78°C.) to trap any unreacted trifluoromethane sulfenyl chloride, and then through a scrubbing system to remove the vented hydrogen chloride gas. Residual liquid was transferred to a flask and distilled to give 1-trifluoromethylthio-3,3-dimethyl-2-butanone, b.p. 65°C./10mmHg.

Analysis: Calculated: %C, 41.99; %H, 5.54; Found: %C, 42.0; %H, 5.4.

EXAMPLE 5

Preparation of 1-trifluoromethylthio-3,3-dimethyl-2-butanone oxime.

Using the method of example 2, 1-trifluoromethylthio-3,3-dimethyl-2-butanone was reacted with hydroxylamine hydrochloride to provide the desired oxime, m.p. 94.5° to 96°C.

Analysis: Calculated for $C_7H_{12}F_3NOS$: %C, 39.05; %H, 5.62; %N, 6.51; Found: %C, 39.1; %H, 5.7; %N, 6.4.

EXAMPLE 6

Preparation of 1-trifluoromethylthio-3,3-dimethyl-2-butanone-0-methylcarbamoyloxime (Process A)

A mixture of 1-trifluoromethylthio-3,3-dimethyl-2-butanone oxime (0.044 mole) from example 5, methyl isocyanate (0.048 mole) and 3 drops of triethylamine in 50 ml. of dichloromethane was heated at reflux temperature overnight. The solvent was removed by evaporation under vacuum. The residual oil was recrystallized from a mixture of petroleum ether and diethyl ether to give the purified sample of 1-trifluoromethylthio-3,3-dimethyl-2-butanone-0-methylcarbamoyloxime, m.p. 82.5° to 84°C. The structure of the product was confirmed by elemental and spectral analyses.

EXAMPLE 7

Preparation of 1-trifluoromethylthio-3,3-dimethyl-2-butanone-0-methylcarbamoyloxime (Process B)

To a cold (0.5°C.) benzene solution of phosgene (23.2 g of 12.5% solution, i.e. 0.03 mole phosgene) was added dimethylaniline (0.03 mole). To the cold mixture was added 1-trifluoromethylthio-3,3-dimethyl-2-butanone oxime (0.03 mole) from example 5 and 60 ml of benzene. The reaction mixture was stirred for 2 hours at room temperature. Aqueous methylamine (0.03 mole) was then added to the reaction mixture. The reaction mixture was then washed with water and dried. Filtration to remove the drying agent was followed by evaporation of the solvents under vacuum to provide a residue which was purified by chromatography on silica gel and recrystallization. The product is 1-trifluoromethylthio-3,3-dimethyl-2-butanone-0-methylcarbamoyloxime by spectral comparison of the product with the spectral characteristics of the product of example 6.

What is claimed is:

1. A compound of the formula

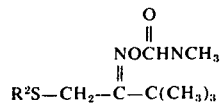

wherein $R^2$ is $CF_3-$ or $CF_2H-$.

2. The compound 1-difluoromethylthio-3,3-dimethyl-2-butanone-0-methylcarbamoyloxime according to claim 1.

3. The compound 1-trifluoromethylthio-3,3-dimethyl-2-butanone-0-methylcarbamoyloxime according to claim 1.

* * * * *